United States Patent
Novak et al.

(10) Patent No.: US 6,864,686 B2
(45) Date of Patent: Mar. 8, 2005

(54) HIGH-FREQUENCY SURGICAL DEVICE AND OPERATION MONITORING DEVICE FOR A HIGH-FREQUENCY SURGICAL DEVICE

(75) Inventors: Pavel Novak, Stetten (CH); Konrad Kellenberger, Flurlingen (CH); Felix Daners, Schaffhausen (CH)

(73) Assignee: Storz Endoskop GmbH (DE)

( * ) Notice: Subject to any disclaimer, the term of this patent is extended or adjusted under 35 U.S.C. 154(b) by 159 days.

(21) Appl. No.: 10/273,942

(22) Filed: Oct. 18, 2002

(65) Prior Publication Data

US 2003/0036757 A1 Feb. 20, 2003

Related U.S. Application Data

(60) Continuation-in-part of application No. 09/716,551, filed on Nov. 20, 2000, now abandoned, which is a division of application No. 09/043,304, filed on Mar. 12, 1998, now Pat. No. 6,261,285.

(51) Int. Cl.[7] ............... G01R 31/327; G01R 31/08; G01R 27/26; A61B 18/00
(52) U.S. Cl. ............... 324/419; 324/654; 324/527; 606/34
(58) Field of Search .................. 324/418, 419, 324/547, 421, 546, 522, 523, 654, 527; 700/292; 606/32, 34

(56) References Cited

U.S. PATENT DOCUMENTS

| | | | | |
|---|---|---|---|---|
| 3,253,214 A | * | 5/1966 | Heilweil et al. | 324/419 |
| 3,346,855 A | * | 10/1967 | Bishop | 340/644 |
| 3,822,398 A | * | 7/1974 | Rovnyak | 324/419 |
| 4,028,615 A | * | 6/1977 | Jansen et al. | 324/419 |
| 5,133,711 A | | 7/1992 | Hagen | |
| 5,204,633 A | * | 4/1993 | Ahladas et al. | 324/654 |
| 5,742,513 A | * | 4/1998 | Bouhenguel et al. | 700/286 |

FOREIGN PATENT DOCUMENTS

| | | |
|---|---|---|
| DE | 3151991 | 1/1981 |
| DE | 3942998 | 7/1991 |
| JP | 272194/89 | 4/1991 |

* cited by examiner

*Primary Examiner*—Anjan K. Deb
(74) *Attorney, Agent, or Firm*—St. Onge Steward Johnston & Reens LLC

(57) ABSTRACT

A high-frequency surgical device encompassing control electronics that control a power unit which utilizes a high-frequency transformer that is the only galvanic separation between the supply voltage and the patient/user unit.

12 Claims, 2 Drawing Sheets

HIGH-FREQUENCY SURGICAL DEVICE AND OPERATION MONITORING DEVICE FOR A HIGH-FREQUENCY SURGICAL DEVICE

PRIORITY DOCUMENT

The present application is a continuation-in-part of U.S. patent application Ser. No. 09/716,551, filed Nov. 20, 2000 abandoned, which is a divisional of U.S. patent application Ser. No. 09/043,304, filed Mar. 12, 1998, now U.S. Pat. No. 6,261,285, issued Jul. 17, 2001.

FIELD OF THE INVENTION

The present invention relates to a high-frequency (HF) surgical and operation monitoring device for high-voltage relays and a process for monitoring the operation of high-voltage relays for surgical devices.

BACKGROUND OF THE INVENTION

HF-surgical devices are well known and German A-documents 3151991, 3911416 or 3942.998 are referred to by way of example. Moreover, reference is explicitly made to these printed publications for the explanation of all details not described in detail herein or other technical design of HF-surgical devices.

Known HF-surgical devices, like other electro-medical devices, have a number of problems. For instance, electro-medical devices require galvanic separation between the primary-side power supply and the patient/user unit. This galvanic separation generally occurs in HF-surgical devices by means of a separation transformer. The separation transformer may be either a transformer connected immediately to the primary alternating voltage, or may be a component of a primary timed combinational circuit unit.

High performance high-frequency surgical devices generally have an output power of at least 400 W. Depending upon the efficiency of the transformer, this generally requires a transformer of at least 600VA to power the surgical device.

Therefore, the primary transformer, utilized as a separation transformer, must be very large and heavy. If however, a combinational primary circuit unit is employed, the required transformer may be relatively lightweight, because usually frequencies between 50 and 100 kHz are utilized. However, a disadvantage in utilizing this type of device is the comparatively high cost of the device, and the physical size of the device is still an issue.

A second problem with high-frequency surgical devices is that many times there are several high-frequency generators and several outlets depending on the mode of operation, for instance; cutting or coagulating, bipolar, monopolar, etc. This may mean that a particular outlet may be connected to a number of various high-frequency generators for various procedures. However, in order not to endanger the patient or the physician/user, it is important that the high-frequency energy is only switched to the selected outlet.

For switching between the outlets and the generators, a relay matrix having make contacts as operating contacts is utilized so that non-utilized outlets are not connected to the generator electronics when the device is switched off. Device failures may occur such that an outlet that should be switched off is incorrectly connected to the generator electronics. This may occur if, for instance, a contact of the relay sticks or jams. Errors causing the relay to fail to close, such as, if the relay coil is interrupted or has a short circuit, are much less frequent.

In addition, relays characteristically require a relatively large quantity of power in order to pick up and/or contact. This power must be supplied by an internal power supply, usually by an "auxiliary power supply" for the electronics control unit of the high-frequency surgical device. This in turn, creates a situation where the auxiliary power supply highly loaded. Therefore, it is desirable to reduce the power intake and/or requirements for the relay.

SUMMARY OF THE INVENTION

An object of the present invention is to provide a high-frequency surgical device, which meets the pertinent standards for electro-magnetic devices such as IEC 601 or VDE 0750 without utilizing a separation transformer for galvanic separation of the primary power supply and the user unit.

Moreover another object of the present invention is to provide high-frequency surgical devices with increased safety to the patient and physician/user.

It is a further object of the present invention to provide a device in which the power requirements placed upon the auxiliary power supply and devices are greatly reduced.

The present invention is based on the following understanding: practically every HF-surgical device possesses a high-frequency output transformer for power adaptation between the power final stage and the cutting electrode. The transformer is usually operated with a frequency of between 0.3 Mhz to 1 Mhz. This high-frequency output transformer, however, is not employed in HF-surgical devices for galvanic separation between the primary power supply circuit and the user unit.

However, this HF-output transformer may be utilized as a galvanic separation between the (primary) supply voltage and the patient/user unit. In order to do so, the HF output is designed according to particular standards relating to isolation voltage, air gaps, and leakage distances. In particular, a high-frequency transformer that meets the FFIEC 601 and VDE 0750 standards may be utilized.

High-frequency output transformers are operated with relatively high frequencies, namely usually 0.3 Mhz to 1 Mhz. Therefore, the high-frequency output transformer may be relatively small and lightweight, and therefore less expensive when compared to conventional primary separation transformers or conventional separation transformers in combinational primary circuit units.

The operation elements of the control electronics that a physician/user may come into contact with are galvanically separated from the power unit. This galvanic separation may be effected by means of, for instance; the construction of the casing, employment of switches and/or keys, or by means of transmitters and/or optoelectronic coupling devices. Utilizing these methods facilitates having only a simple universal primary circuit as the internal current supply unit. The measuring signals and also the HF-power may be separated by means of greater insulation from the primary.

This embodiment is advantageous because control signals will no longer have to be separated between the power unit and the control electronics. However, attention must be paid to positioning the components within a casing because a comparatively large leakage distance and air gap is required for the grounded casing.

Preferably the control electronics are provided with a separate primary supply circuit. In order to supply the HF-power amplifier with the required power, the primary supply circuit is provided with a universal rectifier and a controllable DC/DC converter. The DC/DC converter permits covering the whole primary supply voltage range of 100–240 VAC. Preferably the DC/DC converter is capable of drawing a sinusoidal shaped current from the primary. In this event, the voltage is minimally distorted and the RMS current load and therefore the losses in the primary lines are reduced when compared with conventional rectifiers.

Furthermore, the present invention is based on the understanding that a sticking relay contact is a very dangerous kind of failure of the control means for the patient and for the physician/user. Notably, this kind of failure may result in energy being simultaneously applied to two outlets. Therefore, an element of the present invention is that the function-monitoring device determines if the contacts of the relay are being opened.

In order to do so, the function-monitoring device requires the following elements:

a control logic for at least one relay, a controllable voltage supply source, an inductivity measuring switch, and a drive unit which is provided with at least one relay driver.

In addition, the following reed relay properties are utilized:

1. Relays need a large current in the coil only to switch on. As soon as the contact is closed, the current required to maintain the contact closed is much smaller.

2. The relay coil excites a magnetic field whose properties change when the relay armature is closed. For instance, by closing the relay armature, the connection inductivity increases.

3. The inductivity change caused by magnetic saturation effects of the iron saturation is a non-linear effect in the magnetic field. In order to close the relay contact, the windings of the core must be energized. This will cause a magnetic flux in the iron core. If the flux density of the generated magnetic field is high enough, saturation of the iron core will take place. The saturation of the core causes the inductivity to decrease by a relatively large amount.

4. If a relay contact is open, an air gap exists between the contacts. When an air gap exists, the applied magnetic field must be higher than when the contacts are closed (no air gaps exists), in order to reach a flux density that will cause saturation of the core. If the air gap is absent, saturation occurs with a much lower magnetic field strength.

Usually, reed relays are employed as relays that can maintain a sufficiently high voltage over the open contact and still be small in size. An element of the present invention is that it was understood that a property of reed relays, namely that the relay armature does not move a contact via a mechanical coupling like conventional relays do, but rather that the relay armature itself is the contact. In this way the connection inductivity already changes when the contact opens or closes. It is preferred therefore to tune the relay driver to the reed relay.

Advantageously the function monitoring of the high-voltage relays occurs via the respective control current circuit of the relay to be monitored. Therefore, no connections are required to the high-frequency outlets. This is desirable because no high-voltage and/or high-frequency components need to be utilized.

Preferably, an alternating current is superimposed over one outlet of the relay driver. This measure permits easily measuring a change in the inductivity in the relay.

The process for monitoring the function of the high-voltage relay for surgical devices is preferably carried out with the following steps: application of the smallest possible direct voltage with which all the relays connected to the high frequency outlets pick up. Next, superimposition of the direct voltage with alternating voltage that we will label AC1, along with measurement of the alternating current part and storing this measured value. Then application of the largest possible direct voltage with which all the relays connected to the high-frequency outlets close, and superimposition of the direct voltage with the same alternating voltage (AC1). Finally, measurement of the alternating current part, and comparison of the measured alternating current part with the stored alternating current part with the addition of a predetermined minimum value.

The measured alternating current part preferably may be stored by the system.

In another embodiment of the present invention a self-test function is provided in order to detect a malfunction by the function-monitoring device.

BRIEF DESCRIPTION OF THE DRAWINGS

The present invention is made more apparent in the following using preferred embodiments with reference to the drawings, whose figures show the following.

DETAILED DESCRIPTION OF THE DRAWINGS

Figure 1:
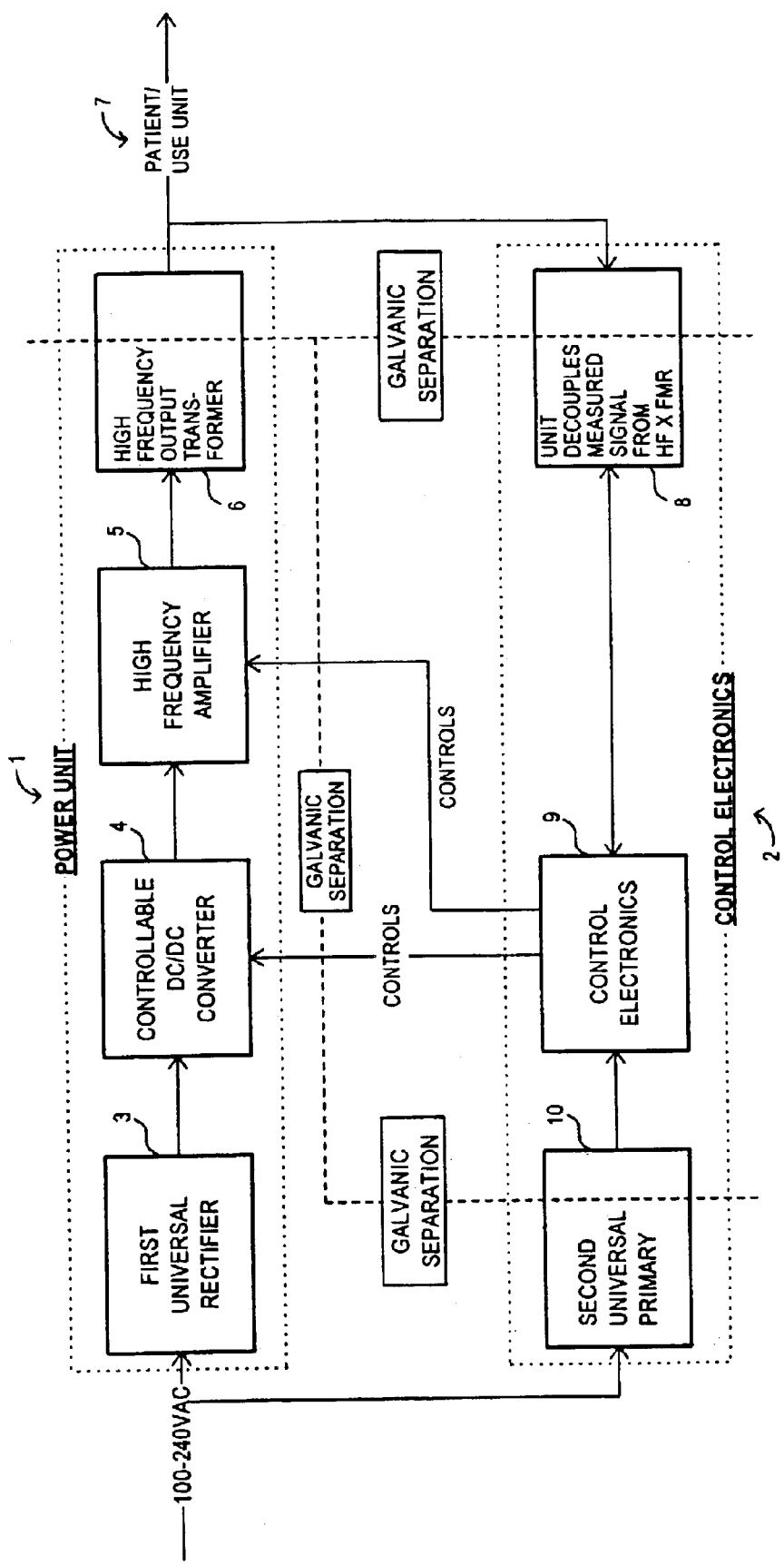
FIG. 1 a block diagram illustrating a high-frequency surgical device according to an advantageous embodiment of the present invention.

In the block diagram of a high-frequency surgical device shown in FIG. 1, 1 stands for the power unit (blocks in the top row) and 2 stands for the control electronics (blocks in the bottom row) (FIG. 1).

The power unit 1 is provided with a universal rectifier 3 to which the primary alternating voltage, which depending on the national standard, may be between 100 and 240V, is applied.

The output connection of the universal rectifier 3 is connected to a controllable DC/DC converter 4, which supplies a high-frequency amplifier 5 with power. The output connection of the power amplifier 5 is connected to a high-frequency output transformer 6, which represents the sole galvanic separation between the primary supply voltage and the patient/user unit (arrow 7).

The control electronics 2 are built in a conventional manner. In particular, a unit 8 is provided, by means of which a measured signal from the HF-output transformer 6 is decoupled. The output signal of unit 8 is applied to a control electronics 9, which control both the controllable DC/DC converter 4 and the HF-power amplifier 5.

A galvanic separation, which usually fills a 4 kV/8 mm leakage distance, is provided. The galvanic separation may be implemented through use of suitable switches or, in particular, membrane switches or, by means of optocouplers and/or transmitters.

Furthermore, a second universal primary part 10, which is designed for low power (i.e.15 W), is provided for the power supply of the control electronics. However, the control electronics may alternately be supplied by an auxiliary power supply voltage, which is supplied by the actual primary supply circuit.

A smaller and lighter high-frequency surgical device is generated by the invented embodiment, in which the galvanic separation between the patient/user unit and the primary supply voltage occurs in the actual primary supply circuit.

Figure 2:
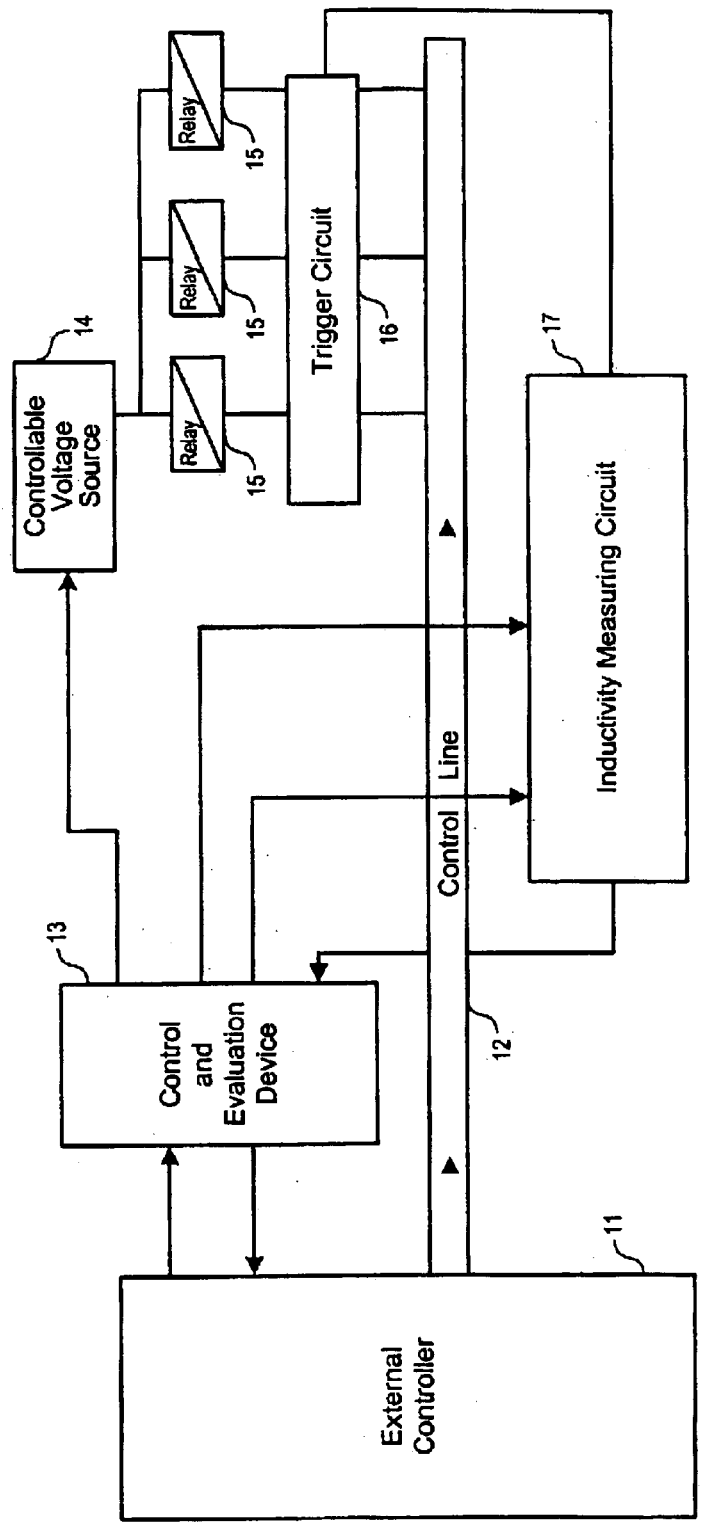
FIG. 2 a block diagram illustrating a function-monitoring device according to an advantageous embodiment of the present invention.

The invented measuring principle for monitoring the function of high-voltage relays for surgical devices as illustrated in FIG. 2, is as follows:

In one advantageous embodiment, a surgical device is provided with multiple outlets, each outlet having a corresponding relay. In order to determine whether the contact of a particular relay closes, the change in inductivity of the relay coil is measured. In order to determine the inductivity, the direct voltage, which is required to build up the magnetic field and to close the contact, is superimposed with a small alternating voltage. The current generated by the alternating voltage is used as a value for determining the inductivity. This permits, for instance, using relays from various manufacturers as the absolute values may differ. Moreover, the circuit does not require expensive components or complicated balancing. It is to be noted however, that this principle works readily only with reed relays.

The change in inductivity is determined in two phases: In this embodiment, the procedure takes approximately 18 ms.

1. Phase: A direct voltage, which does not cause any of the relays pick up, in this case 0.0V, is applied to the relays. This voltage is superimposed with a square wave voltage of 0.5V with 650 Hz. In order to measure the current, the drop in voltage is measured via a 1-ohm precision resistor. The voltage resulting over the resistor is decoupled with a capacitor in order to evaluate only the alternating voltage part. This AC signal is then amplified and rectified with a peak value rectifier. This voltage is then stored with a holding amplifier (i.e. sample and hold).

2. Phase: The largest possible direct voltage, which does not cause any of the relays to close, is applied to the relays. The same voltage is superimposed as in the first phase. A new voltage now sets in at the peak value rectifier, because the inductivity of the open contact has increased. However, this increase in inductivity may be counteracted when the relays are energized, because magnetic flux will cause saturation, which in turn causes the inductivity to dramatically drop. Therefore, it is desired to avoid applying a direct current voltage that will cause the relays to pick up.

The measured voltage is compared with the stored voltage by means of a comparator. If the new value decreases by a predetermined minimum value, the contact has opened correctly. If the voltage changes too little, it is determined that the contact is sticking or that another component is defective.

In this embodiment, the inductivity measuring circuit 17 contains a high-pass filter, an amplifier, a peak value rectifier, a peak detector, a holding amplifier and a comparator. The alternating current is measured via a shunt resistor through which a current flows coming from the selected relay in the trigger circuit 16.

By restricting the DC voltage range to a minimum pick up voltage and a maximum drop-out voltage of the relay, measurement accuracy is improved; simultaneously both these relay parameters are monitored.

Furthermore, it must be taken into account that the relay holding voltage becomes substantially smaller when a contact is interrupted, because the spring force for opening the contact is missing.

The invented circuit can therefore be utilized in such a manner that each relay 15 is tested upon switching off. Therefore, the contact is open after testing and represents the safest state. In this way it is achieved that at no time is HF-energy applied to an outlet that was not switched on.

The circuit can, of course, also analogously be utilized to test the relays 15 when switching on.

As illustrated in FIG. 2, the circuit is set up in such a manner that only one control and evaluation device 13 is required for any number of relays 15. An external controller 11 controls the triggering of any one of the relays 15.

Particular attention must be paid to the fact that the evaluation of the relay state is determined solely via the control current circuit and therefore requires no connection to the HF outlets. In this case, the control and evaluation circuit has four circuit parts:

micro-controller 11;

controllable voltage source 14;

inductivity measuring circuit 17; and trigger circuit 16.

The external controller 11 has an input connection and two output connections so that three data lines are available for communication.

Via one connection, the external controller 11 informs the trigger circuit 16 whether a relay 15 has to be activated or whether a relay 15 has to be tested. The purpose of the other two connections is synchronization and feedback of the test results. Via the data control line 12, the trigger circuit 16 is informed which relays 15 should be switched on.

The circuit can trigger any number of relays 15. In this embodiment, however, only one can be tested at one time. In this embodiment, the external controller 11 is responsible for correctly interpreting the data from the control and evaluation device 13 and selecting the desired relays 15.

In addition, the trigger circuit is set up in such a manner that every first error is detected in the trigger circuit by means of a self-test and transmitted to the external controller 11.

In order to activate a relay 15, the external controller 11 activates the trigger circuit 16, which is informed that one or more relays 15 are to be switched on. On the basis of this signal, the power supply voltage of the relays 15 is raised by the controllable voltage source 14 for 5 ms so that the relays can pick up safely. Subsequently, the power supply voltage is reduced so that only a little more than the holding current flows through each relay coil. The reduction of the power supply voltage occurs, by way of illustration by clocking the direct voltage. The pulse/pause ratio reduces the power. The advantage of this triggering is that there are only small losses in the voltage source and that the overall current consumption drops.

The same signal informs the trigger circuit 16 that a relay 15 is to be tested. Thus, the test mode is always run through upon switching off this signal. It is the responsibility of the external controller 11 to set the right relay 15 and ensure correct, timed triggering.

An error or defect in the trigger circuit 16 could prevent detection of a relay defect. Therefore, it is necessary that a circuit self-test be conducted. This self-test does not require additional components and is conducted automatically. It is not activated from the outside and not detected.

If an error is detected, the outlets of the external controller 11 are closed. In this manner, the external controller 11 can detect a circuit defect.

Although the invention has been described with reference to a particular arrangement of parts, features and the like, these are not intended to exhaust all possible arrangements or features, and indeed many other modifications and variations will be ascertainable to those of skill in the art.

What is claimed is:

1. A function-monitoring device for high-voltage relays for surgical devices comprising:
   a controllable voltage source, for generating a variable voltage;
   a relay trigger circuit, for triggering a relay;
   an inductivity measuring circuit, for measuring the inductivity of the relay; and
   a control logic, for variably applying to the relay a first and a second direct current voltage and superimposing a first and second alternating current voltage over the first and second direct current voltages respectively to generate first and second measured values, and for comparing the first and second measured values to generate a new value, and for comparing the new value with a reference value.

2. The function-monitoring device of claim 1, wherein said trigger circuit is tuned to reed relays.

3. The function-monitoring device of claim 2, wherein the function-monitoring device has no electrical connection to high-frequency outlets of the high voltage to be monitored.

4. The function-monitoring device of claim 1, wherein the first direct current voltage applied to the relay is 0.0V.

5. The function-monitoring device of claim 1, wherein the second direct current voltage applied to the relay is the maximum voltage that can be applied to the relay without the relay closing.

6. The function-monitoring device of claim 1, wherein said control logic conducts a self-test prior to or following the application of the direct and alternating current voltages to the relay.

7. A method for monitoring the function of high-voltage relays for surgical devices comprising the steps of:
   application of a first direct voltage, which does not cause magnetic saturation of the relays and does not cause the relays to close;
   superimposition of an alternating current voltage onto the first direct current voltage to create a first measured value;
   application of a second direct current voltage, which is the largest possible direct current voltage with which no relay contacts will close;
   superimposition of an alternating current voltage onto the second direct current voltage to create a second measured value;
   comparison of the second measured value with the first measured value to create a new value; and
   comparison of the new value with a minimum reference value.

8. The method according to claim 7 wherein the first direct current voltage applied is zero volts.

9. The method according to claim 7, further comprising the step of conducting a self-test prior to or following the process for monitoring the function of high-voltage relays for surgical devices.

10. A function-monitoring device for high-voltage relays for surgical devices comprising:
    a direct current voltage source;
    an alternating current voltage source;
    an inductivity measuring circuit;
    a logic controller;
        wherein said logic controller applies a first direct current voltage to the relay and superimposes a first alternating current voltage over the first direct current voltage and generates a first measured value;
        and said logic controller applies a second direct current voltage to the relay and superimposes the first alternating current voltage over the second direct current voltage and generates a second measured value;
        and compares the first and second measured values to generate a new value, which is then compared to a reference value.

11. The function-monitoring device of claim 10, wherein said logic controller is tuned to reed relays.

12. The function-monitoring device of claim 11, wherein the function-monitoring device has no electrical connection to high-frequency outlets of the high voltage to be monitored.

* * * * *